United States Patent
Christe et al.

(10) Patent No.: US 9,439,952 B2
(45) Date of Patent: Sep. 13, 2016

(54) RAPID-ACTING INSULIN COMPOSITIONS

(71) Applicant: Eli Lilly and Company, Indianapolis, IN (US)

(72) Inventors: Michael Edward Christe, Pendleton, IN (US); Thomas Andrew Hardy, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/781,342

(22) PCT Filed: May 4, 2015

(86) PCT No.: PCT/US2015/029010
§ 371 (c)(1),
(2) Date: Sep. 30, 2015

(87) PCT Pub. No.: WO2015/171484
PCT Pub. Date: Nov. 12, 2015

(65) Prior Publication Data
US 2016/0129087 A1  May 12, 2016

Related U.S. Application Data

(60) Provisional application No. 61/990,402, filed on May 8, 2014.

(51) Int. Cl.
*A61K 38/28* (2006.01)
*A61K 31/5585* (2006.01)
*A61K 31/5575* (2006.01)

(52) U.S. Cl.
CPC ........... *A61K 38/28* (2013.01); *A61K 31/5575* (2013.01); *A61K 31/5585* (2013.01)

(58) Field of Classification Search
CPC .................................................. A61K 38/28
See application file for complete search history.

(56) References Cited

U.S. PATENT DOCUMENTS

| 8,324,157 | B2 | 12/2012 | Olsen et al. |
| 2005/0282903 | A1 | 12/2005 | Wade et al. |
| 2015/0065423 | A1 | 3/2015 | Laulicht et al. |

FOREIGN PATENT DOCUMENTS

| EP | 0001124 | 3/1979 |
| EP | 2500020 | 9/2014 |
| WO | 03094956 | 11/2003 |
| WO | 2010023666 | 3/2010 |
| WO | 2010149772 | 12/2010 |
| WO | 2012080362 | 6/2012 |
| WO | 2015120457 | 8/2015 |

OTHER PUBLICATIONS

Blaise, S., et al., "Cathodal Iontophoresis of Treprostinil Induces a Sustained Increase in Cutaneous Blood Flux in Healthy Volunteers," J. Clin. Pharmacol., vol. 53, Issue 1, pp. 58-66 (2012).
Gille, A., et al., "Nicotinic Acid: Pharmacological Effects and Mechanisms of Action," Annu. Rev. Pharmacol. Toxicol., vol. 48, pp. 79-106 (2008).
Mathier, M., et al., "Subcutaneous Treprostinil in Pulmonary Arterial Hypertension: Practical Considerations," J. Heart Lung Transplant., vol. 29, pp. 1210-1217 (2010).
McSwain, C., et al., "Dose Proportionality of Treprostinil Sodium Administered by Continuous Subcutaneous and Intravenous Infusion," J. Clin. Pharmacol., vol. 48, pp. 19-25 (2008).
Menon, R., et al., "Insulin Absorption Accelerated by α-Adrenergic Blockade at Injection Site," Diabetes Care, vol. 10, No. 4, pp. 470-472 (1987).
Moriarty, R., et al., "The Intramolecular Asymmetric Pauson-Khand Cyclization as a Novel and General Stereoselective Route to Benzindene Prostacyclins: Synthesis of UT-15 (Treprostinil)," J. Org. Chem, vol. 69, pp. 1890-1902 (2004).
Owens, D., et al., "The Influence of Aprotinin on Regional Absorption of Soluble Human Insulin," Br. J. Clin. Pharmac., vol. 25, pp. 453-456 (1988).
Vora, J., et al., "Relationship Between Absorption of Radiolabeled Soluble Insulin, Subcutaneous Blood Flow, and Anthropometry," Diabetes Care, vol. 15, No. 11, pp. 1484-1493 (1992).
Wade, M., et al., "Absolute Bioavailability and Pharmacokinetics of Treprostinil Sodium Administered by Acute Subcutaneous Infusion," J. Clin. Pharmacol., vol. 44, pp. 83-88 (2004).
Williams, G., et al., "Subcutaneous Aprotinin Causes Local Hyperaemia," Diabetologia, vol. 24, pp. 91-94 (1983).
Williams, G., et al., "Prostaglandin E1 Accelerates Subcutaneous Insulin Absorption in Insulin-Dependent Diabetic Patients," Diabetic Medicine, pp. 109-113 (1984).
NDA 21-272, RemodulinTM, Medical Review, available at http://www.accessdata.fda.gov/drugsatfda_docs/nda/2002/21-272_Remodulin.cfm.
NDA 21-272, RemodulinTM, Clinical Pharmacology & Biopharmaceutics Review(s), available at http://www.accessdata.fda.gov/drugsatfda_docs/nda/2002/21-272_Remodulin.cfm.
Remodulin® (treprostinil) Injection Package Insert.

*Primary Examiner* — Amber D Steele
(74) *Attorney, Agent, or Firm* — Matthew T. Lord

(57) ABSTRACT

The invention is a composition of human insulin or insulin analog that includes treprostinil and that has faster pharmacokinetic action than commercial formulations of existing insulin analog products.

19 Claims, No Drawings

SEQUENCE LISTING

```
<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: synthetic construct

<400> SEQUENCE: 3
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25              30

<210> SEQ ID NO 4
<211> LENGTH: 30
<212> TYPE: PRT
<213> ORGANISM: Artificial Sequence
<220> FEATURE:
<223> OTHER INFORMATION: synthetic construct

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25              30

<210> SEQ ID NO 5
<211> LENGTH: 30
<212> TYPE: PRT
<213> ORGANISM: Artificial Sequence
<220> FEATURE:
<223> OTHER INFORMATION: synthetic construct

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25              30
```

RAPID-ACTING INSULIN COMPOSITIONS

The present invention is a pharmaceutical insulin composition for use in the treatment of diabetes to counteract post-prandial blood glucose excursions and for acute treatment of hyperglycemia. The composition includes human insulin or an insulin analog and treprostinil. The composition has a faster uptake of insulin from injection sites than existing commercial insulin compositions, and it is sufficiently stable for long-term storage. The composition is useful for providing meal-time insulin activity or an acute treatment for hyperglycemia when insulin is needed.

The time-action profile of insulin is important for controlling post-prandial blood glucose levels. In healthy individuals, the pancreas secretes a spike of insulin in response to absorbed food, which results in increased blood insulin levels within several minutes. In individuals with type 1 diabetes and in certain individuals with type 2 diabetes, insulin must be administered. However, administered insulin enters blood slowly. Too slow of onset and inadequate release of insulin at the beginning of a meal leads to hyperglycemia after the meal. Too long duration of action and excessive insulin between meals causes postprandial hypoglycemia and may contribute to weight gain.

There have been previous efforts to reduce the time-action of insulin products. Early efforts to develop such products included the development of novel "rapid-acting" insulin analogs, like insulin lispro (HUMALOG®) and insulin aspart (NOVOLOG®), which achieve rapid action through changes in the amino acid sequences from the sequences of the amino acid chains in human insulin. Another analog, insulin glulisine (APIDRA®), lacks zinc and does not form stabilizing hexamers. APIDRA® therefore requires an additional stabilizing agent, polysorbate 20. The rapid-acting insulin analogs became available in the 1990s and early 2000s. Even with so-called rapid-acting insulin analogs, the maximum insulin level is not reached until 50-90 minutes following the injection. This is slower than insulin is released by a normally functioning pancreas and does not always match carbohydrate absorption profiles.

Another avenue to achieve rapid action that has been explored is to search for ingredients that improve the time action profile of insulin when provided in combination with insulin. For example, in the 1980s it was stated that prostaglandin $E_1$ accelerates insulin absorption when administered in combination with insulin. Williams, et al., 1 Diabetic Med. 109-13 (1984). Prostaglandin $E_1$, however, is chemically unstable, minimally aqueously soluble, and rapidly catabolized, which are not desirable traits for use in insulin compositions. Another agent stated to accelerate insulin absorption is the protease inhibitor aprotinin, but aprotinin is unsuitable for repeated administration due to its potential to induce immunological reactions. D. R. Owens, et al., 25 BR. J. CLIN. PHARMAC. 453-456 (1988). More recently, it has been stated that a faster onset of action compared with existing insulin therapies can be achieved by adding a nicotinic compound, such as nicotinamide, and the amino acid arginine, and optionally glutamic acid. See U.S. Pat. No. 8,324,157.

Nevertheless, there remains a need for insulin compositions, intended for use at meal-time, that: have more rapid uptake of insulin from the injection site and more rapid onsets of action than existing insulin products; are stable chemically and physically during prolonged storage to minimize safety risks and to assure dose accuracy and efficacy; do not result in unacceptable levels of injection site pain; and/or require a minimal number of ingredients and/or excipients to achieve improvements in time action while maintaining sufficient stability.

The present invention seeks to provide formulations which meet these needs. In particular, the present invention provides formulations of insulin and treprostinil which have more rapid uptake of insulin into the blood. The present invention also provides a more rapid onset of action and/or absorption than existing commercial insulin products. In addition, the formulations of the present invention are sufficiently stable. In addition, the administration of the formulations of the present invention does not result in unacceptable injection site pain. The formulations of the present invention achieve these effects while using a minimal number of additional components.

According to a first aspect of the present invention, there is provided a composition comprising an insulin and treprostinil.

In an embodiment, the insulin is selected from the group consisting of human insulin, or a rapid-acting structural variant, mutant, or analog of human insulin, such as insulin lispro, insulin aspart and insulin glulisine. In a preferred embodiment, the insulin is insulin lispro. In an embodiment, the insulin lispro concentration is from about 40 to about 500 IU/mL. Preferably, the insulin lispro concentration is either 100 IU/mL or 200 IU/mL.

The amount of treprostinil in the composition must be sufficient to result in an onset of action and/or absorption that is faster than that of the insulin formulation with no treprostinil. The concentration of treprostinil used in the compositions of the present invention ranges from about 0.01 to about 30 µM, particularly from about 0.05 to about 26 µM, about 0.05 to 0.3 µM, about 0.1 to 0.5 µM, about 0.3 to 1.5 µM, about 0.5 to 5.1 µM, about 1.5 to 5.9 µM, about 5.1 to 12.8 µM, about 5.9 to 20 µM, about 12.8 to 24 µM, about 20 to 26 µM, or about 26 to 30 µM, particularly either about 0.05, 0.1, 0.3, 0.5, 1.5, 5.1, 5.9, 12.8, 20, 24 or 26 µM. The insulin and treprostinil are present in a fixed dose combination.

In an embodiment of the present invention, the composition comprises one or more preservatives. In a preferred embodiment, the one or more preservatives are selected from the group consisting of phenol, meta-cresol, and benzyl alcohol. Preferably, the preservative is meta-cresol. In an embodiment, the meta-cresol concentration is from about 2.5 mg/mL to about 3.8 mg/mL. Preferably, the meta-cresol concentration is about 3.15 mg/mL.

In an embodiment of the present invention, the composition comprises a tonicity agent. In an embodiment, the tonicity agent is selected from the group consisting of glycerol and sodium chloride. In a preferred embodiment, the tonicity agent is glycerol. In another preferred embodiment, the glycerol concentration is from about 5 to about 20 mg/mL. Preferably, the glycerol concentration is about 16 mg/mL.

In an embodiment, the composition may further comprise one or more stabilizing agents. In a preferred embodiment, the one or more stabilizing agents are selected from the group consisting of zinc, sodium chloride, calcium chloride, and arginine. Preferably, the stabilizing agent is zinc. Zinc oxide may be provided in the compositions in an amount sufficient to provide the desired number of zinc atoms. The compositions of certain embodiments of the present invention include zinc at a ratio of about 2-4 zinc atoms per six molecules of insulin. Certain preferred compositions will have about 2.5-3.5 atoms of zinc per six molecules of insulin. In certain embodiments, the concentration of zinc is from about 0.00525 mg/mL to about 0.131 mg/mL Preferably, when the insulin concentration is about 100 IU/mL, the zinc concentration is about 0.0197 mg/mL.

In an embodiment, the composition may further comprise a buffering agent. In certain embodiments, the buffering agent is selected from the group consisting of phosphate buffers, such as dibasic sodium phosphate, TRIS (2-amino-2-hydroxymethyl-propane-1,3-diol; Tromethamine) or sodium acetate. In certain preferred embodiments, the buffering agent is phosphate or TRIS.

In certain embodiments of the invention, the pH of the composition is about 7.0 to about 7.8. Preferably, the pH is about 7.4.

In an embodiment, the composition comprises insulin lispro in a concentration from about 40 to about 500 IU/mL, treprostinil in a concentration from about 0.01 to about 30 µM, meta-cresol in a concentration from about 2.5 to about 3.8 mg/mL, glycerol in a concentration from about 5 to about 20 mg/mL, zinc in a concentration from about 0.00525 to about 0.131 mg/mL, and the pH of the composition is from about 7.0 to about 7.8. In a preferred embodiment, the insulin concentration is about 100 IU/mL, treprostinil concentration is from about 0.05 to about 26 µM, zinc concentration is about 0.0197 mg/mL, meta-cresol concentration is about 3.15 mg/mL, glycerol concentration is about 16 mg/mL, and the pH of the composition is about 7.4.

According to a second aspect of the present invention, there is provided a method of treating diabetes comprising administering to a human in need thereof an effective dose of any of the aforementioned compositions.

According to a third aspect of the present invention, there is provided any of the aforementioned compositions for use as a medicament. In an embodiment, the use of the composition is for use in the treatment of diabetes. The present invention also provides the use of any of the aforementioned compositions for the manufacture of a medicament for the treatment of diabetes.

According to a fourth aspect of the present invention, there is provided an article of manufacture comprising any of the aforementioned compositions. In an embodiment, the article of manufacture is a multi-use vial. In another embodiment, the article of manufacture is a re-usable pen injector. In another embodiment, the article of manufacture is a pump device for continuous subcutaneous insulin infusion therapy.

In another aspect, the present invention provides for insulin for use in combination with treprostinil. In another aspect, the present invention provides for treprostinil for use in combination with insulin.

The onset of action and/or absorption profile for an insulin product can be measured in a number of ways. For example, serum insulin concentrations can be measured to calculate pharmacokinetic parameters relevant to time action, such as the time to maximum insulin concentration (Tmax), as well as the maximum insulin concentration (Cmax), and the time to reach the total insulin exposure, which is measured as the total area under the insulin concentration curve from 0 to infinity (AUCinf). Similarly, the glucose infusion rate (GIR) required to maintain normal serum glucose concentrations after insulin administration provides a direct measure of the pharmacodynamic action of the insulin. The present invention provides for a more rapid uptake of insulin into the blood and/or more rapid onset of action than existing commercial insulin products as reflected, for example, in shorter Tmax, shorter time to reach 50% of the Cmax (early 50% Tmax), shorter time for 50% of the Cmax to be cleared (late 50% Tmax), shorter time to reach 10%, 20% or 50% of the AUCinf, shorter time to maximal GIR or 50% maximal GIR, and/or other pharmacokinetic and/or pharmacodynamic parameters that would reflect more rapid absorption or action of the insulin.

When used herein, the term "composition" refers to a fixed dose combination of insulin and treprostinil, wherein the insulin, treprostinil, and any other ingredients or excipients, are combined in a single combined formulation.

When used herein, "insulin" means human insulin or a rapid-acting structural variant, mutant, or analog of human insulin that has the functional activity of but faster onset of action than human insulin. Particular rapid-acting analogs of human insulin are insulin lispro, insulin aspart, and insulin glulisine. Insulin for commercial products may be produced using recombinant DNA methods or by chemical synthesis. Recombinant methods are well-known and are strongly preferred. A molecule of human insulin (CAS No. 11061-68-0) consists of two amino acid chains, A and B, whose sequences are well-known.

The human insulin A-chain has the following sequence of amino acids:

```
                                            (SEQ ID NO: 1)
Gly Ile Val Glu Gln Cys Cys Thr Ser Ile Cys Ser

Leu Tyr Gln Leu Glu Asn Tyr Cys Asn.
```

The human insulin B-chain has the following sequence of amino acids:

```
                                            (SEQ ID NO: 2)
Phe Val Asn Gln His Leu Cys Gly Ser His Leu Val

Glu Ala Leu Tyr Leu Val Cys Gly Glu Arg Gly Phe

Phe Tyr Thr Pro Lys Thr.
```

The chains are joined by two disulfide bonds: CysA7-CysB7 and CysA20-CysB19. The A-chain has an intra-chain disulfide bond at CysA6-CysA11. Human insulin has the empirical formula $C_{257}H_{383}N_{65}O_{77}S_6$ and a molecular weight of 5808.

Insulin lispro (sometimes referred to as KPB), the drug substance in HUMALOG®, is identical to human insulin in terms of its primary amino acid sequence except for an inversion of the natural proline-lysine sequence on the B-chain at positions 28 and 29 ($28^B$-L-Lysine-$29^B$-L-proline human insulin). Insulin lispro (CAS No. 133107-64-9) has been shown to be equipotent to human insulin on a molar basis but its effect after subcutaneous injection is more rapid and of shorter duration than that of injected soluble human insulin. HUMALOG® contains m-cresol as a preservative and a stabilizer agent, a tonicity modifier (glycerin), a buffering agent (dibasic sodium phosphate), a stabilizer (zinc oxide) and pH adjustment for the vehicle.

A molecule of insulin lispro consists of the human insulin A-chain (SEQ ID NO. 1) cross-linked with the insulin lispro B-chain, whose amino acid sequence is given by SEQ ID NO: 3, below:

```
                                            (SEQ ID NO: 3)
Phe Val Asn Gln His Leu Cys Gly Ser His Leu Val

Glu Ala Leu Tyr Leu Val Cys Gly Glu Arg Gly

Phe Phe Tyr Thr Lys Pro Thr.
```

The chemical formula of insulin lispro is $C_{257}H_{383}N_{65}O_{77}S_6$ and its molecular weight is approximately 5808. One unit of insulin lispro is equivalent to 0.0347 mg insulin lispro.

Insulin aspart (CAS No. 116094-23-6), the drug substance in NOVOLOG®, is another rapid-onset insulin analog. Its structure consists of the A-chain of human insulin (SEQ ID NO: 1) and a B-chain in which the Pro at B28 is replaced with Asp (Pro-B28-Asp human insulin), as reflected in the following amino acid sequence:

```
                                          (SEQ ID NO: 4)
Phe Val Asn Gln His Leu Cys Gly Ser His Leu Val

Glu Ala Leu Tyr Leu Val Cys Gly Glu Arg Gly Phe

Phe Tyr Thr Asp Lys Thr.
```

Insulin aspart ($28^B$ aspartic acid-human insulin) has the empirical formula $C_{256}H_{381}N_{65}O_{79}S_6$ and a molecular weight of about 5826. One unit of insulin aspart corresponds to 6 nmol, corresponding with 0.035 mg salt-free anhydrous insulin aspart.

Insulin glulisine (CAS No. 207748-29-6), the drug substance in APIDRA®, is yet another rapid-onset insulin analog. A molecule of insulin glulisine consists of human insulin A-chain (SEQ ID NO. 1) and a modified B-chain (Asn-B3-Lys, Lys-B29-Glu) compared with human insulin, as reflected in the following amino acid sequence: Phe Val Lys Gln His Leu Cys Gly Ser His Leu Val Glu Ala Leu Tyr Leu Val Cys Gly Glu Arg Gly Phe Phe Tyr Thr Pro Glu Thr (SEQ ID NO: 5).

Insulin glulisine ($3^B$-lysine-$29^B$-glutamic acid-human insulin) has the empirical formula $C_{258}H_{384}N_{64}O_{78}S_6$ and a molecular weight of 5823. One unit of insulin glulisine corresponds approximately to 0.0349 mg of insulin glulisine.

The following scheme depicts the amino acid sequences and disulfide bonds of human insulin and of the drug substances in rapid-acting insulin products that are presently approved for use in treating meal-time excursions of blood glucose:

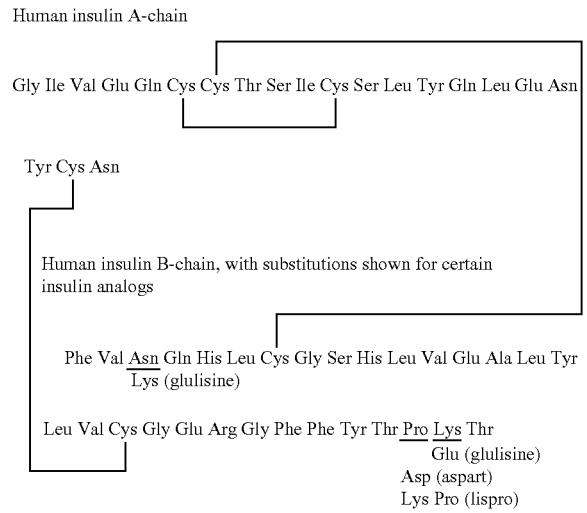

The compositions of the present invention have concentrations of insulin between 0.24 and 3 mM (40-500 IU/mL; 1.4 mg/mL-17.5 mg/mL). The compositions of the present invention are likely to have specific concentrations of 40, 100, 200, 300, 400, and 500 IU/mL (1.4, 3.5, 7, 10.5, 14, and 17.5 mg/mL). Preferred compositions have concentrations of 100 IU/mL or 200 IU/mL.

The improvements in the time action profile of the above-referenced insulin analogs demonstrated in the present invention are achieved through the use of small amounts of the prostacyclin analog treprostinil (CAS No. 81846-19-7). The chemical name of treprostinil is (1R,2R,3aS,9aS)-[[2,3,3a,4,9,9a-Hexahydro-2-hydroxy-1-[(3S)-3-hydroxyoctyl]-1H-benz[f]inden-5-yl]oxy]acetic acid. It has a molecular weight of 390.52 and a molecular formula of $C_{23}H_{34}O_5$. Treprostinil is the active ingredient in the commercial drug products sold under the trade names Remodulin®, Tyvaso® and Orenitran™, which are indicated for the treatment of pulmonary arterial hypertension to diminish symptoms associated with exercise (Remodulin®) and to improve exercise ability (Tyvaso® and Orenitran™). Tyvaso® and Orenitran™ are, respectively, inhalation and oral dosage forms, and Remodulin® is indicated for subcutaneous or intravenous use as a continuous infusion. Remodulin® is currently available in 1, 2.5, 5 and 10 mg/mL dosage strengths, and each mL also contains 3 mg metacresol, 6.3 mg sodium citrate, either 5.3 mg (1, 2.5 and 5 mg/mL strengths) or 4.0 mg (10 mg/mL strength) sodium chloride, and water for injection.

The route of administration for the compositions of the present invention will typically be by self-administered subcutaneous injection, e.g., by use of a syringe or a pen device, or by continuous subcutaneous insulin infusion therapy with an insulin pump device, though intravenous, intradermal, or intraperitoneal routes may also be used. Preferably, the route of administration is by self-administered subcutaneous injection. The dose of active agent injected will be determined by the patient in consultation with the patient's physician.

The compositions are sterile when first produced. When the composition is provided in a multi-use vial or cartridge, an anti-microbial preservative compound or mixture of compounds that is compatible with the other components of the formulation is typically added at sufficient strength to meet regulatory and pharmacopoeial anti-microbial preservative requirements. See U.S. Pharmacopeia Monographs. Insulin lispro injection. USP29-NF24; British Pharmacopeia Monographs 2008 Volume III: Insulin aspart injection; U.S. Pharmacopeia Monographs. Insulin assays; and U.S. Pharmacopeia general chapters. USP29-NF24. Rockville, Md.: U.S. Pharmacopeial Convention; 2005. Antimicrobial effectiveness testing; pp. 2499-2500. Preferred preservatives are aryl acids and phenolic compounds, or mixtures of such compounds. Effective concentrations can be ascertained readily using the methods referenced above. Preservatives most commonly used in insulin products are phenol, m-cresol, and benzyl alcohol. Present commercial compositions, for example, contain 3.15 mg/mL m-cresol (HUMALOG® and APIDRA®), 1.72 mg/mL m-cresol and 1.50 mg/mL phenol (NOVOLOG®), and 2.5 mg/mL m-cresol (HUMULIN® R U-500).

It is desirable to approximately match the tonicity (i.e., osmolality) of body fluids at the injection site as closely as possible when administering the compositions because solutions that are not approximately isotonic with body fluids can produce a painful stinging sensation when administered. Thus, it is desirable that the compositions be approximately isotonic with body fluids at the sites of injection. If the osmolality of a composition in the absence of a tonicity agent is sufficiently less than the osmolality of the tissue (for blood, about 300 mOsmol/kg; the European Pharmacopeial requirement for osmolality is >240 mOsmol/kg), then a tonicity agent should generally be added to raise the tonicity of the composition to about 300 mOsmol/kg. Typical tonicity agents are glycerol (glycerin) and sodium chloride. The amount of tonicity agent to add is readily determined using standard techniques. Remington: The Science and Practice of Pharmacy, David B. Troy and Paul Beringer, eds., Lippincott Williams & Wilkins, 2006, pp. 257-259; Remington: Essentials of Pharmaceutics, Linda Ed Felton, Pharmaceutical Press, 2013, pp. 277-300.

If necessary, the composition may further comprise one or more stabilizing agents, such as zinc, sodium chloride, calcium chloride, and arginine. Zinc is a commonly used stabilizing agent, and zinc oxide may be added to provide the desired number of zinc atoms. Some commercial insulin compositions have about 2.4 atoms of zinc per six molecules of insulin (HUMULIN® R U-500), and some have about 3.0 atoms of zinc per six molecules of insulin (HUMALOG®, NOVOLOG®).

If necessary, a buffering compound may be included. Examples of such buffering compounds are phosphate buffers, such as dibasic sodium phosphate, TRIS or sodium acetate. Phosphate or TRIS buffers are preferred.

The pH for commercial insulin formulations is usually in the range of 7.2 to 7.6, with 7.4±0.1 as a common target pH. The pH of the present invention is typically 7.0 to 7.8 and it is adjusted using physiologically appropriate acids and bases, typically hydrochloric acid 10% and sodium hydroxide 10%. Preferably, the pH is about 7.4.

In an embodiment, the onsets of action and/or absorption profiles of the compositions of the present invention are at least about 20% faster than compositions that contain the same insulin but that do not contain treprostinil, as measured, for example, by: pharmacokinetic parameters, including but not limited to Tmax, early 50% Tmax, late 50% Tmax, Cmax, and/or time to reach 10%, 20% or 50% of the total AUCinf; and/or pharmacodynamic parameters, such as time to reach maximal GIR or time to reach 50% maximal GIR. In another embodiment, the onsets of action and/or absorption profiles of the compositions of the present invention are at least about 25% faster than compositions that contain the same insulin but that do not contain treprostinil, as measured, for example by pharmacokinetic and/or pharmacodynamic parameters, including those referenced above. In another embodiment, the onsets of action and/or absorption profiles of the compositions of the present invention are at least about 30% faster than compositions that contain the same insulin but that do not contain treprostinil, as measured, for example by pharmacokinetic and/or pharmacodynamic parameters, including those referenced above.

The present invention also contemplates the following non-limiting list of embodiments, which are further described elsewhere herein:

A pharmaceutical composition comprising an insulin, treprostinil, one or more preservatives, a tonicity agent, one or more stabilizing agents, and optionally, a buffering agent.

A pharmaceutical composition comprising an insulin, treprostinil, one or more preservatives, a tonicity agent, one or more stabilizing agents, and optionally, a buffering agent, wherein the insulin is selected from the group consisting of human insulin, insulin lispro, insulin aspart and insulin glulisine, the one or more preservatives are selected from the group consisting of phenol, meta-cresol, and benzyl alcohol, the tonicity agent is selected from the group consisting of glycerol and sodium chloride, the one or more stabilizing agents are selected from the group consisting of zinc, sodium chloride, calcium chloride, and arginine and the buffering agent is selected from the group consisting of phosphate, TRIS or sodium acetate.

A pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is glycerol, the stabilizing agent is zinc, and the buffering agent is TRIS.

A pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is glycerol, the stabilizing agent is zinc, and the buffering agent is phosphate.

A pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is sodium chloride, the stabilizing agent is zinc, and the buffering agent is TRIS.

A pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is glycerol, the stabilizing agent is zinc, and the buffering agent is phosphate.

A pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is sodium chloride, the stabilizing agent is zinc, and the buffering agent is phosphate, and wherein the insulin lispro concentration is from about 40 to about 500 IU/mL, treprostinil concentration is from about 0.01 to about 30 µM, zinc concentration is from about 0.00525 mg/mL to about 0.131 mg/mL, meta-cresol concentration is from about 2.5 mg/mL to about 3.8 mg/mL, and glycerol concentration is from about 5 to about 20 mg/mL.

A pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is sodium chloride, the stabilizing agent is zinc, and the buffering agent is phosphate, and wherein the insulin lispro concentration is about 100 IU/mL, treprostinil concentration is from about 0.05 to about 26 µM, zinc concentration is about 0.0197 mg/mL, meta-cresol concentration is about 3.15 mg/mL, and glycerol concentration is about 16 mg/mL.

A pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is sodium chloride, the stabilizing agent is zinc, and the buffering agent is TRIS, and wherein the insulin lispro concentration is about 100 IU/mL, treprostinil concentration is from about 0.05 to about 26 µM, zinc concentration is about 0.0197 mg/mL, meta-cresol concentration is about 3.15 mg/mL, and glycerol concentration is about 16 mg/mL, and wherein the pH of the composition is about 7.4.

A pharmaceutical composition comprising any of the aforementioned compositions wherein the onset of action and/or absorption profile of the composition is at least about 20% faster than compositions that contain the same insulin but that do not contain treprostinil, as measured, for example, Tmax, early 50% Tmax, late 50% Tmax, Cmax, time to reach 10%, 20% or 50% of the total AUCinf, time to reach maximal GIR, and/or or time to reach 50% maximal GIR. A pharmaceutical composition comprising any of the aforementioned compositions wherein the onset of action and/or absorption profile of the composition is at least about 25% faster than compositions that contain the same insulin but that do not contain treprostinil, as measured, for example, by Tmax, early 50% Tmax, late 50% Tmax, Cmax, time to reach 10%, 20% or 50% of the total AUCinf, time to reach maximal GIR, and/or time to reach 50% maximal GIR. A pharmaceutical composition comprising any of the aforementioned compositions wherein the onset of action and/or absorption profile of the composition is at least about 30% faster than compositions that contain the same insulin but that do not contain treprostinil, as measured, for example, by Tmax, early 50% Tmax, late 50% Tmax, Cmax, time to reach 10%, 20% or 50% of the total AUCinf, time to reach maximal GIR, and/or time to reach 50% maximal GIR.

A pharmaceutical composition comprising any of the aforementioned compositions wherein the composition is administered by subcutaneous injection.

A method of treating diabetes comprising administering to a human in need thereof an effective dose of a pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is either glycerol sodium chloride, the stabilizing agent is zinc, and the buffering agent is phosphate or TRIS, and wherein the onset of action and/or absorption profile of the composition is at least about 20% faster than compositions that contain the same insulin but that do not contain treprostinil, as measured, for example, by Tmax, early 50% Tmax, late 50% Tmax, Cmax, time to reach 10%, 20% or 50% of the total AUCinf, time to reach maximal GIR and/or time to reach 50% maximal GIR. A method of treating diabetes comprising administering to a human in need thereof an effective dose of a pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is either glycerol or sodium chloride, the stabilizing agent is zinc, and the buffering agent is phosphate or TRIS, and wherein the onset of action and/or absorption profile of the composition is at least about 25% faster than compositions that contain the same insulin but that do not contain treprostinil, as measured, for example, by Tmax, early 50% Tmax, late 50% Tmax, Cmax, time to reach 10%, 20% or 50% of the total AUCinf, time to reach maximal GIR, and/or time to reach 50% maximal GIR. A method of treating diabetes comprising administering to a human in need thereof an effective dose of a pharmaceutical composition comprising an insulin, treprostinil, one or more preservatives, a tonicity agent, one or more stabilizing agents, and optionally, a buffering agent, wherein the insulin is insulin lispro, the preservative is meta-cresol, the tonicity agent is either glycerol or sodium chloride, the stabilizing agent is zinc, and the buffering agent is phosphate or TRIS, and wherein the onset of action and/or absorption profile of the composition is at least about 30% faster than compositions that contain the same insulin but that do not contain treprostinil, as measured, for example, by Tmax, early 50% Tmax, late 50% Tmax, Cmax, time to reach 10%, 20% or 50% of the total AUCinf, time to reach maximal GIR, and/or time to reach 50% maximal GIR.

The invention is further illustrated by the following examples, which are not to be construed as limiting.

Stability Study

A stability study is performed to assess the stability of insulin lispro when co-formulated with treprostinil. Stability samples are prepared by combining a formulation of insulin lispro (Lilly Material #QA415Q) and Remodulin® (United Therapeutics, Batch 922017), a commercially available product which contains 1 mg/mL treprostinil, 3 mg/mL m-cresol, 6.3 mg sodium citrate, 5.3 mg/mL sodium chloride, and water for injection. Each milliliter of the formulation placed on stability contains insulin lispro 100 units, 16 mg glycerin, 2.13 mg dibasic sodium phosphate, 3.18 mg m-cresol, 0.0197 mg zinc ion, 0.01 mg treprostinil, 0.063 mg sodium citrate, 0.053 mg sodium chloride, 0.0024 mg sodium hydroxide, and Milli-Q water. The pH is adjusted to a final pH of 7.4 by addition of aqueous solutions of hydrochloric acid 1 N and/or sodium hydroxide 1 N.

The solution is filtered using 50 ml Steriflip Vacuum filter with 0.22 μm PES membrane (Cat#: SCGP00525, EMD Millipore, Billerica, Md.) and distributed into 7 mL scintillation vials with screw-top white urea closure with cork-backed aluminum foil liners (vials and caps: Cat#:03-340-4A, Kimble Chase, Rockwood, Tenn.), incubated at 5° C., 25° C., 30° C. and 37° C. respectively, and pulled for analysis at initial, 1 week, 2 week, 3 week, 4 week and 36 day time points. Samples are also pulled for analysis at 44, 54 and 66 day time points for solutions incubated at 5° C., 25° C. and 30° C.

High pressure size-exclusion chromatography (HP-SEC) is used to assess protein stability and quantify high molecular weight species in each formulation using an Agilent 1200 system with UV detection at 214 nm (Agilent Technologies, Santa Clara, Calif.). Each sample (5 μL) is injected onto a Tosoh TSKgel G2000SWx1 column (Tosoh Bioscience LLC, King of Prussia, Pa.; 3000 mm×7.8 mm) and separated at a flow rate of 0.5 mL/min using a mobile phase containing 10 mM sodium phosphate, 10% acetonitrile (ACN), and 300 mM NaCl at pH 7.4. Percentage of high molecule weight (% HMW) is calculated by dividing chromatographic HMW peak areas at 214 nm by total peak area.

SEC results (% HMW) are given in the table below.

| Time Point | Storage Condition | | | |
| --- | --- | --- | --- | --- |
| (days) | 5° C. | 25° C. | 30° C. | 37° C. |
| 0 | 0.09 | 0.09 | 0.09 | 0.09 |
| 7 | 0.10 | 0.12 | 0.14 | 0.20 |
| 14 | 0.11 | 0.15 | 0.18 | 0.24 |
| 21 | 0.13 | 0.16 | 0.28 | 0.43 |
| 28 | 0.13 | 0.18 | 0.26 | 0.52 |
| 36 | 0.145 | 0.163 | 0.333 | 0.927 |
| 44 | 0.076 | 0.368 | 0.676 | N/A |
| 54 | 0.138 | 0.463 | 0.78 | N/A |
| 66 | 0.364 | 0.356 | 0.525 | N/A |

HMW formation is less than 1% for all samples out to 36 days at 37° C. and 66 days at 30° C., which indicates low risk of instability.

Reversed phase high-performance liquid chromatography (RP-HPLC) analysis is performed to assess protein purity at the stability time points using an Agilent 1200 system with UV detection at 214 nm (Agilent Technologies, Santa Clara, Calif.). Each sample (5 μL) is separated at 60° C. by using a 4.6×100 mm (3.5 μm) Symmetry Shield RP18 (Waters, Huntingdon Valley, Pa.) at a flow rate of 0.9 mL/min with mobile phase A (0.1% trifluoroacetic acid (TFA) in water) and mobile phase B (0.1% TFA in acetonitrile). Gradient of mobile phase B at 0, 3, 5, 20, 25, 27 and 30 min is 10, 10, 20, 45, 90, 10 and 10%, respectively.

Insulin concentrations are calculated by integration of the insulin peak area and comparison to an insulin lispro standard. Results, reported in IU/mL, are given below.

| Time Point | Storage Condition | | | |
|---|---|---|---|---|
| (days) | 5° C. | 25° C. | 30° C. | 37° C. |
| 0 | 103.2 | 103.2 | 103.2 | 103.2 |
| 14 | 101.8 | 105.3 | 104.2 | 103.2 |
| 21 | 102.7 | 107.2 | 105.2 | 103.2 |
| 28 | 102.9 | 105.8 | 103.4 | 102.2 |
| 36 | 103.4 | 105.4 | 102.4 | 102.6 |
| 44 | 103.1 | 103.7 | 103.4 | N/A |
| 54 | 102.6 | 103.7 | 104.5 | N/A |
| 66 | 102.8 | 105.0 | 104.6 | N/A |

Minimal, if any, insulin loss is observed for all samples out to 36 days at 37° C. and 66 days at 30° C.

Percentage of sample outside of main peak is calculated by dividing chromatographic main peak area by total peak area. Results (% outside of main peak) are given below.

| Time Point | Storage Condition | | | |
|---|---|---|---|---|
| (days) | 5° C. | 25° C. | 30° C. | 37° C. |
| 0 | 0.4 | 0.4 | 0.4 | 0.40 |
| 14 | 0.3 | 1.4 | 1.5 | 2.40 |
| 21 | 0.5 | 1.2 | 1.5 | 2.35 |
| 28 | 0.7 | 1.4 | 2.0 | 2.93 |
| 36 | 0.5 | 1.1 | 1.8 | 2.29 |
| 44 | 0.8 | 1.6 | 2.5 | N/A |
| 54 | 1.1 | 1.9 | 2.6 | N/A |
| 66 | 1.2 | 2.3 | 3.2 | N/A |

The percent outside of the main peak area is less than 3% for all samples at 37° C. for 36 days and less than 3.5% for all samples at 30° C. for 66 days, which is acceptable for insulin formulations.

Pharmacokinetic and Pharmacodynamic Studies

Fifteen diabetic (alloxan induced), castrated, male Yucatan miniature swine (average age 20 months old and average body weight of 42 kgs) with previously fitted vascular access ports are used. The diabetic animals are housed individually and have ad lib access to fresh water at all times. They are fed two meals per day of house diet S-9 and receive appropriate maintenance basal and prandial insulin twice per day to manage their diabetic condition.

Test articles (Formulations A, B and C in the table below) are formulated and shipped overnight on cold packs to the test site. Humalog insulin control is 100 IU/mL commercial material stored at the test site.

| Formulation Name | Formulation Composition |
|---|---|
| Insulin lispro + treprostinil 1 ng (Formulation A) | 94 U/mL insulin lispro (3.5 mg/mL) 13 ng/mL treprostinil (~1 ng/pig or 0.026 ng/kg) 7 mM sodium phosphate 16 mg/mL glycerin 3.15 mg/mL m-cresol 0.3 mM zinc pH 7.4 |
| insulin lispro + treprostinil 10 ng (Formulation B) | 93 U/mL insulin lispro (3.5 mg/mL) 128 ng/mL treprostinil (~10 ng/pig or 0.26 ng/kg) 7 mM sodium phosphate 16 mg/mL glycerin 3.15 mg/mL m-cresol 0.3 mM zinc pH 7.4 |
| insulin lispro + treprostinil 400 ng (Formulation C) | 93 U/mL insulin lispro (3.5 mg/mL) 5 μg/mL treprostinil (~400 ng/pig or 10 ng/kg) 7 mM sodium phosphate 16 mg/mL glycerin 3.15 mg/mL m-cresol 0.3 mM zinc pH 7.4 |
| Humalog | 100 U/mL insulin lispro 1.88 mg/mL dibasic sodium phosphate 16 mg/mL glycerin 3.15 mg/mL meta-cresol 0.3 mM zinc pH 7.4 |

The test articles are stored refrigerated until time of dosing and then returned to the refrigerator after dosing of all animals is complete. During the dosing period the test articles remain in an insulated box when not being withdrawn from.

The study is a four-way cross over design. This design allows for each individual animal to receive each of the three test articles and control insulin by dosing one test article each study date (4 dates each 7 days apart).

The day prior to study, animals are fed half their daily ration and receive 0.2 U/kg Humalog Mix 75/25 Insulin as their morning maintenance administration. All study animals are food-fasted overnight and do not receive their evening insulin or meal prior to drug administration on study day.

On the morning of study, all animals are placed into slings for restraint and have their vascular access ports accessed (equipped for blood sampling) and checked for patency. The animals are randomly placed into treatment groups (4 groups n=3-4 per group yields n=15 per treatment prior to any exclusions). After two baseline blood samples are collected (−30 and −20 min), the animals are returned to their pens and are fed ~300 g S-9 diet. Two animals are excluded from the insulin lispro+treprostinil 10 ng treatment group for failure to meet the inclusion criteria of baseline blood glucose above 200 mg/dL, and one animal is excluded from the data analysis of that group due to predose insulin values >10,000 pM, yielding n=12 for that treatment group. One animal is excluded from the insulin lispro+treprostinil 1 ng treatment group for failure to meet the inclusion criteria of baseline blood glucose above 200 mg/dL, yielding n=14 for that treatment group.

Twenty minutes after the presentation of the fully consumed meal, the animals are injected with test article 0.2 U/kg (based on the insulin concentration, average of 9 Units/pig) subcutaneously in the flank (0 min) with a Terumo insulin syringe (0.5 ml ½" needle). All study animals have ad libitum access to clean, fresh water throughout the remaining blood collection period.

Blood pressure is assessed by Cardell Monitor (using veterinary cuff on the tail) at −30 and 0 (predose) minutes for baseline and then 30 and 60 minutes post dose. Three sequential measurements are taken at each time point +/−5 minutes. Data presented are the average of the three readings per individual pig.

Serial blood samples (2.0 mL each) are collected from each animal at the following time points: −30, −20 (then immediately Fed), 0 (just before dose), 5, 10, 15, 30, 45, 60, 75, 90, 105, 120, 150, 180, 240, and 360 minutes following the subcutaneous (sc) dosing.

No adverse events are observed for the duration of the experiment. Blood glucose is monitored in real time with handheld glucometers and all animals are routinely observed for clinical signs of hypoglycemia. Blood pressure is recorded at −30 and 0 minutes for baseline values and then monitored 30 and 60 minutes post dose to assess any incidence induced hypotension. No significant changes occur. No local injection site reactions are noted.

Blood samples (anticoagulant: none [serum]) are maintained at ambient temperature for at least 30 minutes but no more than 2 hours to allow for clotting. Serum is then separated by centrifugation and divided into two aliquots and stored frozen at approximately −70° C.

Serum glucose concentrations are determined using an automated Cobas c311 Clinical Chemistry Analyzer (Roche Diagnostics, Indianapolis, Ind.). Oneway Analysis of Variance followed by Dunnett's test of group mean comparison is performed via JMP 9 Statistical Discovery by SAS on glucose in comparison to Humalog control with significance at $p \leq 0.05$. Serum glucose concentrations (mg/dL) after treatment with the control and test formulations (0.2 U/kg at time 0) are provided in the table below.

| Time (min) | Humalog AVG | Humalog SE | insulin lispro + 1 ng treprostinil AVG | insulin lispro + 1 ng treprostinil SE | insulin lispro + 10 ng treprostinil AVG | insulin lispro + 10 ng treprostinil SE | insulin lispro + 400 ng treprostinil AVG | insulin lispro + 400 ng treprostinil SE |
|---|---|---|---|---|---|---|---|---|
| −30 | 285.6 | 9.4 | 303.3 | 11.1 | 299.8 | 12.7 | 299.3 | 13.9 |
| −20 | 295.5 | 9.5 | 316.2 | 12.5 | 311.2 | 14.4 | 312.3 | 13.5 |
| 0 | 304.1 | 9.0 | 327.2 | 12.2 | 325.5 | 14.6 | 320.5 | 15.5 |
| 5 | 310.7 | 9.4 | 331.0 | 11.5 | 335.3 | 14.7 | 320.6 | 16.0 |
| 10 | 311.3 | 9.5 | 331.0 | 11.9 | 325.2 | 12.9 | 312.9 | 16.2 |
| 15 | 316.9 | 7.8 | 332.3 | 12.4 | 314.2 | 14.8 | 304.1 | 16.0 |
| 30 | 287.6 | 15.2 | 293.8 | 23.2 | 263.5 | 24.8 | 233.5 | 22.8 |
| 45 | 260.7 | 19.9 | 245.3 | 28.0 | 196.9 | 26.4 | 178.9 | 23.5 |
| 60 | 234.1 | 23.0 | 210.8 | 28.0 | 148.0 | 24.4 | 136.0 | 22.8 |
| 75 | 202.6 | 24.6 | 154.9 | 26.1 | 103.9 | 18.9 | 98.9 | 20.8 |
| 90 | 161.1 | 22.4 | 112.4 | 20.4 | 71.4 | 15.5 | 68.7 | 16.8 |
| 105 | 127.6 | 20.5 | 91.4 | 16.9 | 58.1 | 13.7 | 51.7 | 11.3 |
| 120 | 115.2 | 19.5 | 69.8 | 12.9 | 53.5 | 14.3 | 45.4 | 10.4 |
| 150 | 97.1 | 17.5 | 55.6 | 9.9 | 47.7 | 9.8 | 50.1 | 11.1 |
| 180 | 79.4 | 16.5 | 50.1 | 11.3 | 62.9 | 16.6 | 60.4 | 17.0 |
| 240 | 82.2 | 18.5 | 62.4 | 14.8 | 88.4 | 21.5 | 84.5 | 22.9 |
| 360 | 130.5 | 24.7 | 122.3 | 23.3 | 163.2 | 28.2 | 144.1 | 26.0 |

Insulin plus treprostinil resulted in a dose dependent shift of the glucose lowering response compared to Humalog alone. Insulin plus treprostinil also resulted in a greater magnitude of glucose lowering from baseline than Humalog alone. The mean glucose change from baseline (baseline=average of −30 and −20 min samples) at the median Tmax of Humalog (90 minutes) was −129 mg/dL for Humalog, −197 mg/dL for insulin lispro+1 ng treprostinil, −234 mg/dL insulin lispro+10 ng Treprostinil, and −237 mg/dL insulin lispro+400 ng treprostinil. Mean glucose comparisons using the Dunnett's method demonstrates statistically significant differences between the insulin lispro+ 400 ng treprostinil sample compared to Humalog control as early as 45 min (p=0.0148). By 60 minutes and through 150 minutes the glucose reductions for insulin lispro+400 ng treprostinil and insulin lispro+10 ng treprostinil are statistically different from Humalog controls. There is no discernable or statistical (Dunnett's) difference in mean systolic or diastolic blood pressure at baseline (−30 & 0 min) or after treatment with any of the three doses of insulin lispro+ treprostinil compared to Humalog control.

With respect to pharmacokinetics, insulin levels for all serum PK samples are measured using a total insulin radioimmunoassay (RIA). Lower and upper limits of quantitation for the assay are 20 pM and 5000 pM, respectively. Values below the lower limit of quantitation are assumed to be 20 pM. Non-compartmental pharmacokinetic analyses are performed using Phoenix WinNonlin v6.3.

| Compound | | Tmax (min) | Cmax (nM) | $AUC_{INF}$ (min * nM) | CL/F (mL/min/kg) |
|---|---|---|---|---|---|
| Humalog | Mean | 83.7 | 0.732 | 117 | 11.4 |
| N = 15 | SE | 13.0 | 0.0964 | 11.0 | 1.01 |
| | Median | 90.0 | 0.699 | 106 | 11.3 |
| insulin lispro + | Mean | 75.0 | 0.922 | 127 | 10.1 |
| treprostinil 1 ng | SE | 12.9 | 0.0759 | 9.63 | 0.838 |
| (Formulation A) | Median | 60.0 | 0.898 | 137 | 8.78 |
| N = 14 | | | | | |
| insulin lispro + | Mean | 48.8 | 1.53 | 154 | 8.57 |
| treprostinil 10 ng | SE | 5.58 | 0.247 | 15.4 | 0.711 |
| (Formulation B) | Median | 45.0 | 1.15 | 131 | 9.14 |
| N = 12 | | | | | |
| insulin lispro + | Mean | 49.0 | 1.20 | 144 | 8.95 |
| treprostinil 400 ng | SE | 6.46 | 0.127 | 12.0 | 0.578 |

-continued

| Compound | | Tmax (min) | Cmax (nM) | $AUC_{INF}$ (min * nM) | CL/F (mL/min/kg) |
|---|---|---|---|---|---|
| (Formulation C) | Median | 30.0 | 1.14 | 134 | 8.98 |
| N = 15 | | | | | |

Abbreviations:
Tmax—time to maximal insulin concentration,
Cmax—maximum insulin concentrations,
$AUC_{INF}$—area under the insulin concentration curve from 0 to infinity,
CL/F—clearance/bioavailability.

Combination of insulin lispro with treprostinil produced a dose-dependent shift in the insulin PK profiles, compared to Humalog alone. The median $T_{max}$ values were 90 min, 60 min, 45 min and 30 min respectively for Humalog alone, insulin lispro+treprostinil 1 ng, insulin lispro+treprostinil 10 ng and insulin lispro+treprostinil 400 ng. Addition of treprostinil also led to increases in insulin $C_{max}$ compared to Humalog alone. The earlier, higher $C_{max}$ is consistent with what would be expected for an increased absorption rate. Total insulin exposure ($AUC_{INF}$) was approximately 30% higher for all three groups containing treprostinil, relative to Humalog alone.

Taken together, the shifts in both the insulin PK profiles and the resulting glucose profiles when treprostinil is administered with insulin lispro indicates that treprostinil facilitates more rapid insulin absorption, relative to Humalog alone. The improvements in time action are accomplished without any discernable effects on blood pressure in these animals.

The studies described above demonstrate that addition of small quantities of treprostinil to formulations containing insulin lispro can cause earlier Tmax and higher Cmax in the insulin pharmacokinetic profile as well as earlier and greater glucose lowering effects, and that such formulations are sufficiently stable.

SEQUENCES

Human insulin A-chain
(SEQ ID NO: 1)
Gly Ile Val Glu Gln Cys Cys Thr Ser Ile Cys
Ser Leu Tyr Gln Leu Glu Asn Tyr Cys Asn.

Human insulin B-chain
(SEQ ID NO: 2)
Phe Val Asn Gln His Leu Cys Gly Ser His Leu
Val Glu Ala Leu Tyr Leu Val Cys Gly Glu Arg
Gly Phe Phe Tyr Thr Pro Lys Thr.

Insulin lispro B-chain
(SEQ ID NO: 3)
Phe Val Asn Gln His Leu Cys Gly Ser His Leu
Val Glu Ala Leu Tyr Leu Val Cys Gly Glu Arg
Gly Phe Phe Tyr Thr Lys Pro Thr.

Insulin aspart B-chain
(SEQ ID NO: 4)
Phe Val Asn Gln His Leu Cys Gly Ser His Leu
Val Glu Ala Leu Tyr Leu Val Cys Gly Glu Arg
Gly Phe Phe Tyr Thr Asp Lys Thr.

Insulin glulisine B-chain
(SEQ ID NO: 5)
Phe Val Lys Gln His Leu Cys Gly Ser His Leu
Val Glu Ala Leu Tyr Leu Val Cys Gly Glu Arg
Gly Phe Phe Tyr Thr Pro Glu Thr.

We claim:

1. A pharmaceutical composition comprising an insulin and treprostinil, wherein the treprostinil concentration is from about 0.01 to about 30 µM.

2. The pharmaceutical composition of claim 1, wherein the insulin is selected from the group consisting of human insulin, insulin lispro, insulin aspart and insulin glulisine.

3. The pharmaceutical composition of claim 2, wherein the insulin is insulin lispro.

4. The pharmaceutical composition of claim 1, wherein the insulin concentration is from about 40 to about 500 IU/mL.

5. The pharmaceutical composition of claim 4, wherein the insulin concentration is about 100 IU/mL.

6. The pharmaceutical composition of claim 5, wherein the treprostinil concentration is from about 0.05 to about 26 µM.

7. The pharmaceutical composition of claim 6, further comprising one or more preservatives.

8. The pharmaceutical composition of claim 7, wherein the one or more preservatives are selected from the group consisting of phenol, meta-cresol, and benzyl alcohol.

9. The pharmaceutical composition of claim 8, wherein the preservative is meta-cresol.

10. The pharmaceutical composition of claim 9, wherein the meta-cresol concentration is from about 2.5 mg/mL to about 3.8 mg/mL.

11. The pharmaceutical composition of claim 10, further comprising a tonicity agent.

12. The pharmaceutical composition of claim 11, wherein the tonicity agent is glycerol.

13. The pharmaceutical composition of claim 1, further comprising one or more stabilizing agents.

14. The pharmaceutical composition of claim 13, wherein the stabilizing agent is zinc.

15. The pharmaceutical composition of claim 14, wherein the concentration of zinc is from about 0.00525 mg/mL to about 0.131 mg/mL.

16. The pharmaceutical composition of claim 15, wherein the pH of the composition is from about 7.0 to about 7.8.

17. A pharmaceutical composition comprising:
   a. insulin lispro, in a concentration from about 40 to about 500 IU/mL,
   b. treprostinil, in a concentration from about 0.01 to about 30 µM,
   c. meta-cresol, in a concentration from about 2.5 to about 3.8 mg/mL,
   d. zinc, in a concentration from about 0.00525 to about 0.131 mg/mL, and
   e. the pH of the composition is from about 7.0 to about 7.8.

18. The pharmaceutical composition of claim 17, wherein the:
   a. insulin lispro concentration is about 100 IU/mL,
   b. treprostinil concentration is from about 0.05 to about 26 µM,
   c. meta-cresol concentration is about 3.15 mg/mL,
   d. zinc concentration is from about 0.00525 to about 0.131 mg/mL, and
   e. the pH of the composition is about 7.4.

19. A method of treating diabetes comprising administering to a human in need thereof an effective dose of the pharmaceutical composition of claim 1.

* * * * *